(12) United States Patent
Huang et al.

(10) Patent No.: US 9,358,249 B2
(45) Date of Patent: Jun. 7, 2016

(54) USE OF PATEAMINE A FOR THE TREATMENT OF AGE-RELATED MUSCLE WASTING

(75) Inventors: Jing Huang, Los Angeles, CA (US); Rui Hao, Durham, NC (US); Brett Eugene Lomenick, Los Angeles, CA (US); Nao Jonai, Kanagawa (JP); Simon Diep, Huntington Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/129,539

(22) PCT Filed: Nov. 18, 2009

(86) PCT No.: PCT/US2009/064964
§ 371 (c)(1),
(2), (4) Date: Aug. 4, 2011

(87) PCT Pub. No.: WO2010/059706
PCT Pub. Date: May 27, 2010

(65) Prior Publication Data
US 2011/0288153 A1 Nov. 24, 2011

Related U.S. Application Data

(60) Provisional application No. 61/115,894, filed on Nov. 18, 2008.

(51) Int. Cl.
*A61K 31/425* (2006.01)
*A61K 31/7105* (2006.01)

(52) U.S. Cl.
CPC .... *A61K 31/7105* (2013.01); *G01N 2333/4706* (2013.01); *G01N 2500/10* (2013.01)

(58) Field of Classification Search
None
See application file for complete search history.

(56) References Cited

U.S. PATENT DOCUMENTS

2007/0196850 A1  8/2007  Kennedy et al.
2011/0319338 A1  12/2011  Naora

FOREIGN PATENT DOCUMENTS

EP        1825850 A1    8/2007
WO   WO 2010/059706    5/2010

OTHER PUBLICATIONS

Roth et al. ("Caloric Restriction in Primates and Relevance to Humans", Annals' of New York Academy of Sciences, 928; 2001:305-315).*
Roth et al. ("Effects of Reduced Energy Intake on the Biology of Aging: The Primate Model", European Journal of Clinical Nutrition, 2000; 54(Suppl.3), S15-S20).*
Kitani et al. ("Chronic Treatment of (–) Deprenyl Prolongs the Life Span of Male Fischer 344 Rats: Further Evidence", Life Science, 1993, pp. 281-288, vol. 52).*
Brack al. (EMBO Workshop Report: Molecular and Cellular Gerontology, 2000).*
Kuro-o ("Disease Model: Human Aging", Trends in Molecular Medicine, Apr. 2001).*
"Animal Diversity Web".*
ASHP Statement on Unit Dose Drug Distribution, 1989.*
World Health Organization, Excipients Slides.*
Low et al. ("Inhibition of Eukaryotic Translation Initiation by the Marine Natural Product Pateamine A" Molecular Cell 2005, p. 709-722).*
Lynch Expert Opin. Emerging Drugs 2008 (13) 655-673.*
International Search Report and Written Opinion dated Jul. 27, 2010 issued in PCT/US2009/064964 (WO 2010/059706).
International Preliminary Report on Patentability dated May 24, 2011 issued in PCT/US2009/064964 (WO 2010/059706).
Anisimov et al. (2008) "Mitochondria-targeted plastoquinone derivatives as tools to interrupt execution of the aging program. 5. SkQ1 prolongs lifespan and prevents development of traits of senescence." *Biochemistry (Mosc)*. 73(12):1329-42. Published in Russian in Biokhimiya.
Baker (1993) "Effects of various antioxidants on aging in *Drosophila.*" *Toxicol Ind. Health*. 9: 163-186.
Baur et al. (2006) "Resveratrol improves health and survival of mice on a high-calorie diet." *Nature* 444: 337-42.
Bordeleau et al. (2006) "Functional characterization of IRESes by an inhibitor of the RNA helicase eIF4A." *Nat Chem Biol*. 2: 213-20.
Borra et al. (2005) "Mechanism of human SIRTI activation by resveratrol." *J. Biol. Chem*. 280: 17187-95.
Clardy (2006) "Stopping trouble before it starts." *ACS Chem Biol*. 1: 17-19.
Comfort et al. (1971) "Effect of Ethoxyquin on the Longevity of C3H Mice" *Nature* 229: 254-255.
Curran (2007) "Lifespan Regulation by Evolutionarily Conserved Genes Essential for Viability." *PLoS Genetics* 3(4) e56 : 0479-0487.
Howitz et al. (2003) "Small molecule activators of sirtuins extend *Saccharomyces cerevisiae* lifespan." *Nature* 425: 191-196.
Hu et al. (2000) "Antioxidants may contribute in the fight against ageing: an in vitro model" *Mechanisms of Ageing and Development* 121: 217-230.
Kaeberlein et al. (1999) "The SIR2/3/4 complex and SIR2 alone promote longevity in *Saccharomyces cerevisiae* by two different mechanisms." *Genes Dev*. 13: 2570-80.
Kaeberlein et al. (2005) "Substrate-specific activation of sirtuins by resveratrol." *J. Biol. Chem*. 280: 17038-45.
Khavinson et al. (2000) "Effect of epitalon on the lifespan increase in *Drosophila melanogaster.*" *Mech Ageing Dev*. 120(1-3):141-9.
Merrick (2004) "Cap-dependent and cap-independent translation in eukaryotic systems." *Gene* 332:1-11.
Nakaidze et al. (1978) "Influence of the geroprotector 2-ethyl-6-methyl-3-hydroxypyridine hydrochloride on the lifetime of *Drosophila melanogaster.*" *Biol Bull Acad Sci USSR*. 5(4):505-8.

(Continued)

*Primary Examiner* — Jeffrey S Lundgren
*Assistant Examiner* — Michael Schmitt
(74) *Attorney, Agent, or Firm* — Tom Hunter; Weaver Austin Villeneuve & Sampson LLP

(57) ABSTRACT

In certain embodiments this invention pertains to the discovery that inhibition of the expression and/or activity of eukaryotic initiation factor 4A (eIF4A) inhibits the aging process. Accordingly, in certain embodiments, methods are provided for inhibiting/slowing aging. The methods typically involve administering to a mammal an agent that inhibits the expression and/or activity of eukaryotic initiation factor 4A (eIF4A) in an amount sufficient to inhibit expression or activity of EIF4A, where the agent is not resveratrol.

3 Claims, 5 Drawing Sheets

(56) References Cited

OTHER PUBLICATIONS

Oguro et al. (2003) "RNA aptamers to initiation factor 4A helicase hinder cap-dependent translation by blocking ATP hydrolysis" *RNA* 9: 394-407.

Oxenkrug et al. (2001) "Antioxidant and antiaging activity of N-acetylserotonin and melatonin in the in vivo models." *Ann. N.Y. Acad. Sci.* 939: 190-199.

Pan et al. (2007) "Inhibition of mRNA translation extends life span in Caenorhabditis elegans." *Aging Cell* 6(1):111-119.

Smith et al. (2008) "Age- and calorie-independent life span extension from dietary restriction by bacterial deprivation in Caenorhabditis elegans." *BMC Dev Biol.* 8:49; pp. 1-13.

Valenzano et al. (2006) "Resveratrol prolongs lifespan and retards the onset of age-related markers in a short-lived vertebrate." *Curr Biol.* 16: 296-300.

Wood et al. (2004) "Sirtuin activators mimic caloric restriction and delay ageing in metazoans." *Nature* 430: 686-9.

Di Marco et al. (2012) "The translation inhibitor pateamine A prevents cachexia-induced muscle wasting in mice" *Nature Communications* 3: 896(1-12).

Syntichaki et al. (2007) "Protein Synthesis Is a Novel Determinant of Aging in Caenorhabditis elegans" *Ann. N.Y. Acad. Sci.* 1119: 289-295.

Syntichaki et al. (2007) "eIF4E function in somatic cells modulates ageing in Caenorhabditis elegans" *Nature* 445: 922-926.

\* cited by examiner

Ren-HCV-FF

SEQUENCE LISTING

```
<160> NUMBER OF SEQ ID NOS: 39

<210> SEQ ID NO 1
<211> LENGTH: 23
<212> TYPE: DNA
<213> ORGANISM: Artificial
<220> FEATURE:
<223> OTHER INFORMATION: Target motif for siRNA
<220> FEATURE:
<221> NAME/KEY: misc_feature
<222> LOCATION: (3)..(21)
<223> OTHER INFORMATION: n is A, G, C, or T

<400> SEQUENCE: 1
aannnnnnnn nnnnnnnnnn ntt                                            23

<210> SEQ ID NO 2
<211> LENGTH: 25
<212> TYPE: DNA
<213> ORGANISM: Artificial
<220> FEATURE:
<223> OTHER INFORMATION: Target motif for siRNA
<220> FEATURE:
<221> NAME/KEY: misc_feature
<222> LOCATION: (3)..(23)
<223> OTHER INFORMATION: n is A, G, C, or T

<400> SEQUENCE: 2
aannnnnnnn nnnnnnnnnn nnntt                                          25

<210> SEQ ID NO 3
<211> LENGTH: 23
<212> TYPE: DNA
<213> ORGANISM: Artificial
<220> FEATURE:
<223> OTHER INFORMATION: Target motif for siRNA
<220> FEATURE:
<221> NAME/KEY: misc_feature
```

```
<222> LOCATION: (1)..(1)
<223> OTHER INFORMATION: n is A, G, C, or T
<220> FEATURE:
<221> NAME/KEY: misc_feature
<222> LOCATION: (3)..(23)
<223> OTHER INFORMATION: n is A, G, C, or T

<400> SEQUENCE: 3
nannnnnnnn nnnnnnnnnn nnn                                              23

<210> SEQ ID NO 4
<211> LENGTH: 23
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is A, G, C, or T
<220> FEATURE:
<221> NAME/KEY: misc_feature
<222> LOCATION: (3)..(3)
<223> OTHER INFORMATION: r is A or G
<220> FEATURE:
<221> NAME/KEY: misc_feature
<222> LOCATION: (4)..(20)
<223> OTHER INFORMATION: n is A, G, C, or T
<220> FEATURE:
<221> NAME/KEY: misc_feature
<222> LOCATION: (21)..(21)
<223> OTHER INFORMATION: y is a pyrimidine
<220> FEATURE:
<221> NAME/KEY: misc_feature
<222> LOCATION: (22)..(23)
<223> OTHER INFORMATION: n is a, c, g, or t

<400> SEQUENCE: 4
narnnnnnnn nnnnnnnnnn ynn                                              23

<210> SEQ ID NO 5
<211> LENGTH: 40
<212> TYPE: RNA
<213> ORGANISM: Artificial
<220> FEATURE:
<223> OTHER INFORMATION: RNA aptamer.

<400> SEQUENCE: 5
caggcguuua gccucuaagu aacaggggcc ucccaugagc                            40

<210> SEQ ID NO 6
<211> LENGTH: 40
<212> TYPE: RNA
<213> ORGANISM: Artificial
<220> FEATURE:
<223> OTHER INFORMATION: RNA aptamer.

<400> SEQUENCE: 6
auugaaguag cguuuagguu uagagccgac ccuccccaaa                            40

<210> SEQ ID NO 7
<211> LENGTH: 39
<212> TYPE: RNA
<213> ORGANISM: Artificial
<220> FEATURE:
<223> OTHER INFORMATION: RNA aptamer.

<400> SEQUENCE: 7
aaguuuaguc agacacaaac aacugaccuc cccgcgagc                             39
```

<210> SEQ ID NO 8
<211> LENGTH: 40
<212> TYPE: RNA
<213> ORGANISM: Artificial
<220> FEATURE:
<223> OTHER INFORMATION: RNA aptamer.
<220> FEATURE:
<221> NAME/KEY: misc_feature
<222> LOCATION: (20)..(20)
<223> OTHER INFORMATION: n is a, c, g, or u

<400> SEQUENCE: 8
auaagguuua gccacacgcn cguggccucc ccaauggguc        40

<210> SEQ ID NO 9
<211> LENGTH: 40
<212> TYPE: RNA
<213> ORGANISM: Artificial
<220> FEATURE:
<223> OTHER INFORMATION: RNA aptamer.

<400> SEQUENCE: 9
guuuagcggu ggaugggcaa agcuaccgcc ucccagagcu        40

<210> SEQ ID NO 10
<211> LENGTH: 40
<212> TYPE: RNA
<213> ORGANISM: Artificial
<220> FEATURE:
<223> OTHER INFORMATION: RNA aptamer.

<400> SEQUENCE: 10
gagcguuuag gcacacaccu gcccucccac uacacgagca        40

<210> SEQ ID NO 11
<211> LENGTH: 40
<212> TYPE: RNA
<213> ORGANISM: Artificial
<220> FEATURE:
<223> OTHER INFORMATION: RNA aptamer.

<400> SEQUENCE: 11
aagaguuuag gugucgggcc acacccuccc auuuaucaaa        40

<210> SEQ ID NO 12
<211> LENGTH: 40
<212> TYPE: RNA
<213> ORGANISM: Artificial
<220> FEATURE:
<223> OTHER INFORMATION: RNA aptamer.

<400> SEQUENCE: 12
agguuuaggc ccaucaaacc ugggcccucc caagaccuuc        40

<210> SEQ ID NO 13
<211> LENGTH: 40
<212> TYPE: RNA
<213> ORGANISM: Artificial
<220> FEATURE:
<223> OTHER INFORMATION: RNA aptamer.

<400> SEQUENCE: 13
uaagagcuuu aguugcgaug ugcgcaaccu ccccugagcc        40

<210> SEQ ID NO 14
<211> LENGTH: 40

```
<212> TYPE: RNA
<213> ORGANISM: Artificial
<220> FEATURE:
<223> OTHER INFORMATION: RNA aptamer.

<400> SEQUENCE: 14
caaagcgauu agguccgaga ggucccuccc agccucgcgc                              40

<210> SEQ ID NO 15
<211> LENGTH: 40
<212> TYPE: RNA
<213> ORGANISM: Artificial
<220> FEATURE:
<223> OTHER INFORMATION: RNA aptamer.

<400> SEQUENCE: 15
acauugcauc gacagcugca aggcucccgc cguacaaacc                              40

<210> SEQ ID NO 16
<211> LENGTH: 40
<212> TYPE: RNA
<213> ORGANISM: Artificial
<220> FEATURE:
<223> OTHER INFORMATION: RNA aptamer.

<400> SEQUENCE: 16
acaguacuua accacaagca guacggcucc cagcugagag                              40

<210> SEQ ID NO 17
<211> LENGTH: 40
<212> TYPE: RNA
<213> ORGANISM: Artificial
<220> FEATURE:
<223> OTHER INFORMATION: RNA aptamer.

<400> SEQUENCE: 17
acagguuguu agacaaguag ccaaccggcu cccgccgacc                              40

<210> SEQ ID NO 18
<211> LENGTH: 40
<212> TYPE: RNA
<213> ORGANISM: Artificial
<220> FEATURE:
<223> OTHER INFORMATION: RNA aptamer.

<400> SEQUENCE: 18
acauugcauc gacagcugca aggcucccgc cguacaaacc                              40

<210> SEQ ID NO 19
<211> LENGTH: 40
<212> TYPE: RNA
<213> ORGANISM: Artificial
<220> FEATURE:
<223> OTHER INFORMATION: RNA aptamer.

<400> SEQUENCE: 19
auauagcauu aaaguugcua agcucccaag uaaccucuac                              40

<210> SEQ ID NO 20
<211> LENGTH: 40
<212> TYPE: RNA
<213> ORGANISM: Artificial
<220> FEATURE:
<223> OTHER INFORMATION: RNA aptamer.

<400> SEQUENCE: 20
```
acagcaagua ccaugaagcc uugcggcucc caugaacccc          40

<210> SEQ ID NO 21
<211> LENGTH: 40
<212> TYPE: RNA
<213> ORGANISM: Artificial
<220> FEATURE:
<223> OTHER INFORMATION: RNA aptamer.

<400> SEQUENCE: 21
agaccgacac aaaagcgucg gcgcucccua guaaugaagc          40

<210> SEQ ID NO 22
<211> LENGTH: 40
<212> TYPE: RNA
<213> ORGANISM: Artificial
<220> FEATURE:
<223> OTHER INFORMATION: RNA aptamer.

<400> SEQUENCE: 22
agaccgacau agaagcgucg gcgcucccua guaaugaagc          40

<210> SEQ ID NO 23
<211> LENGTH: 40
<212> TYPE: RNA
<213> ORGANISM: Artificial
<220> FEATURE:
<223> OTHER INFORMATION: RNA aptamer.

<400> SEQUENCE: 23
agaccgacau aaaagcgucg gcgcucccua guaauguagc          40

<210> SEQ ID NO 24
<211> LENGTH: 40
<212> TYPE: RNA
<213> ORGANISM: Artificial
<220> FEATURE:
<223> OTHER INFORMATION: RNA aptamer.

<400> SEQUENCE: 24
ggggaccgcg ccccacaugu gagugaggcc gaaacguaga          40

<210> SEQ ID NO 25
<211> LENGTH: 40
<212> TYPE: RNA
<213> ORGANISM: Artificial
<220> FEATURE:
<223> OTHER INFORMATION: RNA aptamer.

<400> SEQUENCE: 25
ggggaccgcg ccccacaugu gagugaggcc gaaacauaga          40

<210> SEQ ID NO 26
<211> LENGTH: 40
<212> TYPE: RNA
<213> ORGANISM: Artificial
<220> FEATURE:
<223> OTHER INFORMATION: RNA aptamer.

<400> SEQUENCE: 26
ggggaccgcg ccccacaugu gagugagacc gaaacguaga          40

<210> SEQ ID NO 27
<211> LENGTH: 40
<212> TYPE: RNA
<213> ORGANISM: Artificial

```
<220> FEATURE:
<223> OTHER INFORMATION: RNA aptamer.

<400> SEQUENCE: 27
ggggaccgcg ccccacaugu gagugagacc gaaagguaga                               40

<210> SEQ ID NO 28
<211> LENGTH: 40
<212> TYPE: RNA
<213> ORGANISM: Artificial
<220> FEATURE:
<223> OTHER INFORMATION: RNA aptamer.

<400> SEQUENCE: 28
ggggaucgcg ccccacaugu gagugaggcc gaaacguaga                               40

<210> SEQ ID NO 29
<211> LENGTH: 40
<212> TYPE: RNA
<213> ORGANISM: Artificial
<220> FEATURE:
<223> OTHER INFORMATION: RNA aptamer.

<400> SEQUENCE: 29
ggggaccgcg ccccacacgu gagugaggcc gaaacguaga                               40

<210> SEQ ID NO 30
<211> LENGTH: 40
<212> TYPE: RNA
<213> ORGANISM: Artificial
<220> FEATURE:
<223> OTHER INFORMATION: RNA aptamer.

<400> SEQUENCE: 30
ggggaccgcg ccccacaugu gagugaggcc gaaacguagg                               40

<210> SEQ ID NO 31
<211> LENGTH: 40
<212> TYPE: RNA
<213> ORGANISM: Artificial
<220> FEATURE:
<223> OTHER INFORMATION: RNA aptamer.

<400> SEQUENCE: 31
ggggaccgcg ccccacaugu gagugagguc gaaacguaga                               40

<210> SEQ ID NO 32
<211> LENGTH: 40
<212> TYPE: RNA
<213> ORGANISM: Artificial
<220> FEATURE:
<223> OTHER INFORMATION: RNA aptamer.

<400> SEQUENCE: 32
ggggaccgcg ccccacgugu gagugaggcc gaaacauaga                               40

<210> SEQ ID NO 33
<211> LENGTH: 40
<212> TYPE: RNA
<213> ORGANISM: Artificial
<220> FEATURE:
<223> OTHER INFORMATION: RNA aptamer.

<400> SEQUENCE: 33
ggggaccgcg ccccacgugu gagugaggcc gaaacguaga                               40
```

```
<210> SEQ ID NO 34
<211> LENGTH: 30
<212> TYPE: RNA
<213> ORGANISM: Artificial
<220> FEATURE:
<223> OTHER INFORMATION: RNA aptamer.

<400> SEQUENCE: 34
uguggaugau uuguaugauc gcgcauacaa                                        30

<210> SEQ ID NO 35
<211> LENGTH: 30
<212> TYPE: RNA
<213> ORGANISM: Artificial
<220> FEATURE:
<223> OTHER INFORMATION: RNA aptamer.

<400> SEQUENCE: 35
uguggaugau cuguaugauc gcgcauacag                                        30

<210> SEQ ID NO 36
<211> LENGTH: 30
<212> TYPE: RNA
<213> ORGANISM: Artificial
<220> FEATURE:
<223> OTHER INFORMATION: RNA aptamer.

<400> SEQUENCE: 36
uguggaugau uuguaugauc gcgcauacag                                        30

<210> SEQ ID NO 37
<211> LENGTH: 30
<212> TYPE: RNA
<213> ORGANISM: Artificial
<220> FEATURE:
<223> OTHER INFORMATION: RNA aptamer.

<400> SEQUENCE: 37
uguggauggu cuguaugauc gcgcauacag                                        30

<210> SEQ ID NO 38
<211> LENGTH: 30
<212> TYPE: RNA
<213> ORGANISM: Artificial
<220> FEATURE:
<223> OTHER INFORMATION: RNA aptamer.

<400> SEQUENCE: 38
uguggaugaa uguguagauc gcgcuacgca                                        30

<210> SEQ ID NO 39
<211> LENGTH: 30
<212> TYPE: RNA
<213> ORGANISM: Artificial
<220> FEATURE:
<223> OTHER INFORMATION: RNA aptamer.

<400> SEQUENCE: 39
uguggaugaa cgcguagauc gcgcuacgcu                                        30
```

USE OF PATEAMINE A FOR THE TREATMENT OF AGE-RELATED MUSCLE WASTING

CROSS-REFERENCE TO RELATED APPLICATIONS

This application is a 371 National Phase of PCT/US2009/064964, filed on Nov. 18, 2009, which claims benefit of and priority to U.S. Ser. No. 61/115,894, filed on Nov. 18, 2008, both of which are incorporated herein by reference in their entirety for all purposes.

STATEMENT OF GOVERNMENTAL SUPPORT

This invention was made with Government support under R01 CA 124974, awarded by the National Institutes of Health. The Government has certain rights in the invention.

FIELD OF THE INVENTION

The present invention relates to the field of gerontology. More particularly, methods are provided for slowing the onset of symptoms of aging and/or for increasing healthspan.

BACKGROUND OF THE INVENTION

Aging is characterized by a significant increase of the probability of death. In addition, it is typically characterized by a sharp increase in a probability of occurrence of various pathologies and conditions that are not immediately life threatening, but are associated with the aging process. Such pathologies and conditions (symptoms of aging) in mammals include, but are not limited to for example, increased incidence of cancer, loss of sight (cataract), and other sensory deterioration, skin and hair conditions (e.g., alopecia), arthritis, and an age-associated decrease in weight due to the death of muscular and fatty cells, muscle weakness and other mobility deterioration, and the like.

Considerable interest has been devoted to identifying new medications and agents that inhibit aging (e.g., mitigate or slow the onset of one or more symptoms of aging) or improve healthspan.

Vitamins A, C, and E have been observed to increase the duration of life in *Drosophila* (see, e.g., Baker (1993) *Toxicol Ind. Health.*, 9: 163-186). However, hypersaturation of the organism with these vitamins may result in a quick development of hypervitominosis, and may have a negative effect on the functional state of body systems and organs.

There are also known agents, that express geroprotective and antioxidant activity, based on the compound ethoxyquin (santoquin). This compound increased the duration of life of C3H mice, when it was added to the food (see, e.g., Comfort et al. (1971) *Nature.*, 229: 254-255). Longevity of life of the laboratory animals was also increased as a result of the administration of a low toxic water soluble antioxidant 2-ethyl-6-methyl-3-hydroxypyridine chlorohydrate, which is a structural analog of the vitamin B6 (see, e.g., Obukhova (1975) *Uspekhi Khimii* (Russ.), 44: 1914-1925). Insignificant prolongation of life was observed in experiments with 2-mercaptoethanol amine, cysteine, centrophenoxine, butylhydroxyl toluene, glutathione, 3-hydroxypyridine, lactic acid, and gluconic acid (see, e.g., Obukhova and Emmanuel (1988) *Obschie Problemy Biologii* (Russ.)/VINITI, 4: 44-80).

A therapeutic agent, gerovital, that contains procaine has been used as a geroprotective medication (e.g., Mashkovsky (1993) Medicinal drugs (Russ.).—Moscow, Medicina, part 1—chapter 3—p. 375). However, there were incidents of its negative effect on the cardio-vascular functions, disturbances in sleep, anxiety, and muscle aches and joints aches.

Compounds with alleged geroprotective properties, include the endogenous compounds melatonin and N-acetyl-serotonin (NAS). These compounds have antioxidant properties and, according to one of theories on the mechanism of ageing, should have geroprotective effect (see, e.g., Heng-Long Hu et al. (2000) *Mechanisms of Ageing and Development* 121: 217-230). Experiments with C57B1 mice demonstrated that melatonin and its precursor NAS were capable of prolonging the life of the male mice, when they received these compounds from the age of 2 months. However, these compounds were ineffective in experiments with male mice of the same line, when animals received these compounds from the age of 12 months (see, e.g., Oxenkrug et al. (2001) *Ann. N.Y. Acad. Sci.* 939: 190-199).

SUMMARY OF THE INVENTION

In certain embodiments this invention pertains to the discovery that inhibition of the expression and/or activity of eukaryotic initiation factor 4A (eIF4A) inhibits the aging process. Accordingly, in certain embodiments, methods are provided for inhibiting/slowing aging and/or increasing healthspan. The methods typically involve administering to a mammal an agent that inhibits the expression and/or activity of eukaryotic initiation factor 4A (eIF4A) in an amount sufficient to inhibit expression or activity of EIF4A, where the agent is not resveratrol.

In certain embodiments the improved life span and/or health span is characterized by a measure selected from the group consisting of a reduction in frailty, an improvement in function in an age-related disability, the mitigation of a symptom of an age-related disease, and/or a delay in onset of frailty, age-related disability, or age-related disease, relative to the condition of the subject before administration of the compound or derivative or relative to a control population. In certain embodiments the reduction in frailty is characterized by a measure selected from the group consisting of increased strength, weight gain, faster mobility, increased energy, increased levels of activity, increased endurance, and enhanced behavioral response to a sensory cue, wherein the reduction is relative to the condition of the subject before administration of the compound or derivative or relative to a control population. In certain embodiments the reduction in frailty is selected from the group consisting of a decrease in one or more inflammatory biomarkers, an improvement in glucose homeostasis, and a decrease in one of more biomarkers of clotting activation. In certain embodiments the age-related disease is selected from the group consisting of osteoporosis, arthritis, cataracts, macular degeneration, and cardiovascular disease.

In certain embodiments the improved measure of life span and/or health span comprises an improvement in one or more parameters selected from the group consisting of cholesterol level, triglyceride level, high density lipoprotein level, and blood pressure. In certain embodiments the improved measure of life span and/or health span comprises a reduction in, a reversal of, or delay in onset of sarcopenia, relative to the condition of the subject before administration of the compound or relative to a control population.

In one aspect, a method of slowing aging in a mammal and/or increasing healthspan is provided. In certain embodiments the method involves administering to a mammal an amount of an eIF4A inhibitor or pharmaceutically acceptable salt thereof effective to slow aging and/or to improve/increase healthspan.

In another aspect, a method of slowing the progression of age associated hair loss in a mammal is provided, the method comprising administering to a mammal an amount of an eIF4A inhibitor and/or a pharmaceutically acceptable salt thereof effective to slow the progression of age associated hair loss.

In another aspect, a method of slowing the progression of age associated weight loss in a mammal is provided, the method comprising administering to a mammal an amount of an eIF4A inhibitor and/or a pharmaceutically acceptable salt thereof effective to slow the progression of age associated weight loss.

In another aspect, a method of slowing the progression of age associated muscle wasting in a mammal is provided, the method comprising administering to a mammal an amount of an eIF4A inhibitor and/or a pharmaceutically acceptable salt thereof effective to slow the progression of age associated muscle wasting.

In another aspect, a method of slowing the onset of an age associated vision disturbance in a mammal is provided, the method comprising administering to a mammal an amount of an eIF4A inhibitor and/or a pharmaceutically acceptable salt thereof effective to slow the onset of an age associated vision disturbance In another aspect, a method of improving the quality of life of a mammal is provided, the method comprising administering to a mammal an amount of an eIF4A inhibitor and/or a pharmaceutically acceptable salt thereof effective to improve the quality of life of the mammal.

In another aspect, a method for improving the quality of life of a mammal for which slowing aging is desired is provided, the method comprising administering to a mammal for which slowing aging is desired an amount of an eIF4A inhibitor and/or pharmaceutically acceptable salt thereof effective to enhance the quality of life of the mammal In another aspect, a method for improving the quality of life of a human who desires to slow aging is provided, the method comprising administering to a human who desires to slow aging an amount of an eIF4A inhibitor and/or a pharmaceutically acceptable salt thereof effective to enhance the quality of life of the human In another aspect, a method of extending the lifespan of a cell in a mammal is provided, the method comprising administering to a mammal an amount of an eIF4A inhibitor and/or pharmaceutically acceptable salt thereof effective to extending the lifespan of a cell in the mammal.

Methods are also provided for screening for agents that inhibit aging (e.g., mitigate one or more symptoms associated with aging). In various embodiments the methods involve contacting a cell or tissue or animal with a test agent and determining if the test agent inhibits the expression or activity of eIF4A, where an inhibition of eIF4A indicates that the agent is an inhibitor or a candidate inhibitor of aging.

In certain embodiments, the methods and compositions described herein expressly exclude resveratrol, and/or resveratrol derivatives, and/or derivatives of hydrogenated pyrido (4,3-b) indoles as described in U.S. Patent Publication No: 2008/0234310 A1 (which is incorporated herein by reference for the description of derivatives of hydrogenated pyrido (4,3-b) indoles), and/or procaine, and/or melatonin and N-acetylserotonin, and/or any vitamins or vitamin analogues (e.g., as described above in the background of the invention)

DEFINITIONS

The term "geroprotective activity", refers to a biological activity that slows down ageing and/or prolongs life and/or increases or improves the quality of life via a decrease in the amount and/or the level of intensity of pathologies or conditions that are not immediately life-threatening but are associated with the aging process and that are typical for elderly people. Pathologies or conditions that are not life-threatening but are associated with the aging process include, but are not limited to, such pathologies or conditions as loss of sight (cataract), deterioration of the dermatohairy integument (alopecia), and an age-associated decrease in weight due to the death of muscular and/or fatty cells.

A "pharmaceutical formulation" of an eIF4A inhibitor refers to therapeutic form of an eIF4A inhibitor that can be useful for the prophylactic or for the therapeutic application to afford a geroprotective activity for the prophylactics of ageing. In order to make a pharmacological formulation, one or several compounds eIF4A inhibitors (specific inhibitors or general inhibitors) as active ingredient(s) are typically mixed with a pharmacologically acceptable carrier.

The term "health span" refers to the period of time during which an individual meets one or more selected measures of health span. An increase in "health span" refers to an extension in the period of health, according to such measures, as compared to the period of health in a control population. An increase in health span can be measured, e.g., by determining the length of time that an individual continues to meet the selected measure(s) of health span. Alternatively, an increase in health span can be determined by measuring a degree of improvement in one or more selected measures of health span that is correlated with and increase in the length of time that and individual continues to meet the selected measures of health span.

The term "frailty" refers to a condition that can be characterized by (typically, three or more) symptoms selected from weakness, weight loss, slowed mobility, fatigue, low levels of activity, poor endurance; and impaired behavioral response to a sensory cue. Frailty can also be characterized by an increase in one or more inflammatory biomarkers, glucose homeostasis impairment, and/or an increase in one of more biomarkers of clotting activation. Another hallmark of frailty is "sarcopenia," which refers to age-related loss of muscle mass." Frailty can also refer to a reduced ability to maintain homeostasis during the application of a stressor and/or an increase in the time required to return to homeostasis after the application of a stressor. Frailty can also include a decline in mitochondrial function, typically with changes in respiration, and/or morphological aberrations in mitochondria.

An "age-related disability," refers to any physical or mental incapacity associated with normal aging, such as, for example, an age-related decline in near vision.

An "age-related disease" refers an abnormal condition characterized by a disordered or incorrectly functioning organ, part, structure, or system of the body that occurs more frequently in the aged.

BRIEF DESCRIPTION OF THE DRAWINGS

FIG. 1A: Chemical structure of resveratrol. FIG. 1B: Lysate from untreated yeast cells or Hela cell were incubated with resveratrol or vehicle for 1 hr at room temperature, followed by proteolysis, SDS-PAGE, and silver staining. Mass spectrometry identifies the protected protein is eIF4A. FIG. 1C: Western blotting confirms the protection of yeast (TAP-tagged Tifi) eIF4A by resveratrol.

FIG. 3A: Schematic diagram of the bicistronic dual-luciferase mRNA Ren-HCV-FF. FIG. 3B: Resveratrol inhibits cap-dependent translation initiation of *Renilla* luciferase but not eIF4A-independent translation of firefly luciferase. HEK 293 cells transfected with plasmid pcDNA/REN/HCV/FF are treated with different concentration of resveratrol (0, 0.1, 1, 10, 50, 100 µM). Translation of reporter genes was measured 33 hour after transfection using the Dual-Glo luciferase assay (Promega) with an Analyst HT plate reader (Molecular Devices).

DETAILED DESCRIPTION

Figure 1A:
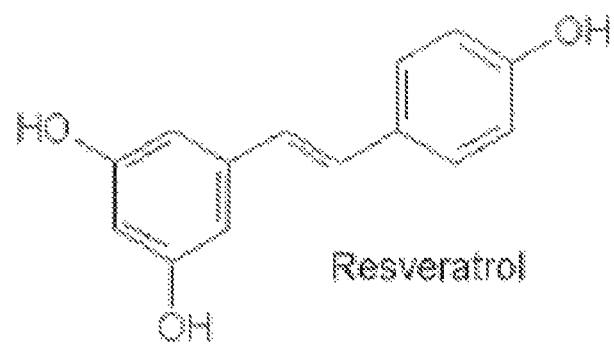
FIGS. 1A-1C illustrate the identification of eIF4A as the molecular target of resveratrol.

In certain embodiments this invention pertains to the discovery that resveratrol (see, FIG. 1A) increases lifespan (slows aging) by inhibiting translation, particularly translation mediated by eukaryotic initiation factor 4A (EIF4A). Based on this discovery it is believed that other translation inhibitors, especially inhibitors that inhibit the expression and/or activity of eIF4A can similarly increase lifespan.

Increasing lifespan (or slowing aging) as described herein refers to slowing aging and/or prolonging lifespan of an individual or cells in an individual, and/or improving quality of life of an individual developing or having a risk of developing age-associated manifestations and/or pathologies.

Accordingly, in certain embodiments, methods are provided for slowing aging (e.g., inhibiting the onset and/or progression of one or more symptoms of aging, and/or increasing lifespan) in a mammal (e.g., a human, or a non-human mammal). The methods typically involve administering to a mammal an agent that inhibits the expression and/or activity of eukaryotic initiation factor 4A (EIF4A) in an amount sufficient to inhibit expression or activity of EIF4A. Typically the agent is an agent other than resveratrol and/or a resveratrol derivative.

Also provided are methods of screening for an agent that inhibits aging. These methods typically involve screening a test agent for the ability to bind to and/or to inhibit the expression and/or activity of eukaryotic initiation factor 4A (eIF4A). The ability of the agent to inhibit the expression and/or activity of eIF4A is an indicator that the agent has an anti-aging activity/effect.

I. Inhibition of eIF4A

The work described herein indicates that resveratrol increases lifespan by inhibiting translation, in particular by inhibiting eIF4A. Based on this discovery, other translation inhibitors (or inhibitors of eIF4A activity) are expected to also have an effect on longevity similar to resveratrol.

Small Molecule eIF4A Inhibitors

Figure 4:
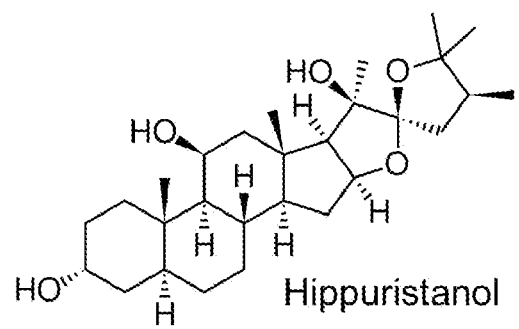
FIG. 4 illustrates the chemical structures of three known eIF4A inhibitors.
Figure 4:
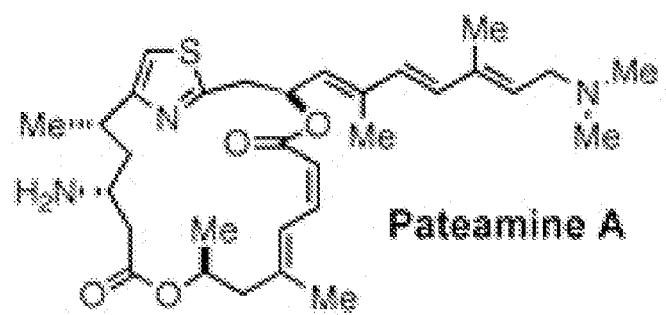
Figure 4:
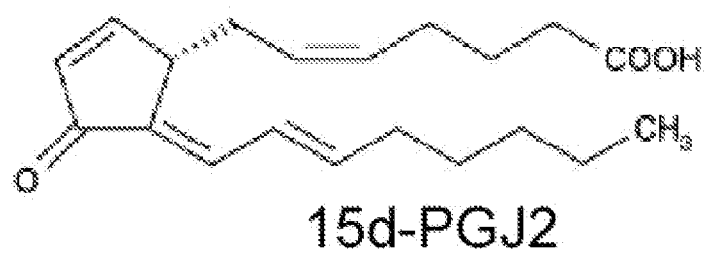

Presently there are at least three chemicals found to selectively inhibit the function of eIF4A (see, FIG. 4). Hippuristanol is a small molecule found in the coral Isis hippurisis. It is reported as a selective and potent inhibitor of eIF4A RNA-binding activity (see, e.g., Bordeleau et al. (2006) *Nat Chem. Biol.*, 2: 213-220). Pateamine A, a potent antiproliferative and proapoptotic marine nature product, inhibits translation by preventing the formation of proper translational initiation complex (see, e.g., Low et al. (2005) *Mol. Cell.* 20(5): 709-722). Another signaling lipid molecule, 15-deoxy-delta 12,14-prostaglandin J2 (15d-PGD2), is able to bind with eIF4A and block the interaction between eIF4A and eIF4G that results in translation of many mRNAs.

Other eIF4A inhibitors can readily be identified using, e.g., the screening methods described herein. In addition to organic molecules, other methods of inhibiting eIF4A expression or activity include, but are not limited to the use of antisense molecules, ribozymes, RNAi inhibition and the like.

Protein Inhibitors.

As described by Yang et al. (2003) Mol. Cell. Biol., 23(1): 26-37, the transformation suppressor Pdcd4 is a novel eukaryotic translation initiation factor 4A binding protein that inhibits translation. Pdcd4 is a novel transformation suppressor that inhibits tumor promoter-induced neoplastic transformation and the activation of AP-1-dependent transcription required for transformation. A yeast two-hybrid analysis revealed that Pdcd4 associates with the eukaryotic translation initiation factors eIF4AI and eIF4AII. Immunofluorescent confocal microscopy showed that Pdcd4 colocalizes with eIF4A in the cytoplasm. Recombinant Pdcd4 specifically inhibited the helicase activity of eIF4A and eIF4F. In vivo translation assays showed that Pdcd4 inhibited cap-dependent but not internal ribosome entry site (IRES)-dependent translation. In contrast, Pdcd4(D418A), a mutant inactivated for binding to eIF4A, failed to inhibit cap-dependent or IRES-dependent translation or AP-1 transactivation. Recombinant Pdcd4 prevented eIF4A from binding to the C-terminal region of eIF4G (amino acids 1040 to 1560) but not to the middle region of eIF4G (amino acids 635 to 1039). In addition, both Pdcd4 and Pdcd4 (D418A) bound to the middle region of eIF4G. The mechanism by which Pdcd4 inhibits translation thus was believed to involve inhibition of eIF4A helicase, interference with eIF4A association-dissociation from eIF4G, and inhibition of eIF4A binding to the C-terminal domain of eIF4G. Pdcd4 binding to eIF4A is linked to its transformation-suppressing activity, as Pdcd4-eIF4A binding and consequent inhibition of translation are required for Pdcd4 transrepression of AP-1.

Accordingly, in certain embodiments, Pdcd4 and active fragments thereof are contemplated for use in the methods described herein (e.g., to inhibit EIF4A to increase lifespan and/or healthspan). In various embodiments the use of full-length Pdcd4 is contemplated. In certain embodiments, Pdcd4 fragments capable of binding EIF4A are contemplated. In various embodiments the Pdcd4 protein or fragments can bear one or more protecting groups (e.g., amide at the carboxyl terminus, acetyl at the amino terminus, and the like).

Antisense Approaches.

EIF4A expression can be downregulated or entirely inhibited by the use of antisense molecules. An "antisense sequence or antisense nucleic acid" is a nucleic acid that is complementary to the coding eIF4A mRNA nucleic acid sequence or a subsequence thereof. Binding of the antisense molecule to the eIF4A mRNA interferes with normal translation of the eIF4A transcription factor.

Thus, in accordance with certain embodiments of this invention, antisense molecules include oligonucleotides and oligonucleotide analogs that are hybridizable with eIF4A messenger RNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of eIF4A polypeptides.

In the context of this invention, the term "oligonucleotide" refers to a polynucleotide formed from naturally-occurring bases and/or cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species that are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

In one embodiment, the internucleotide phosphodiester linkage is replaced with a peptide linkage. Such peptide nucleic acids tend to show improved stability, penetrate the cell more easily, and show enhances affinity for their target. Methods of making peptide nucleic acids are known to those of skill in the art (see, e.g., U.S. Pat. Nos. 6,015,887, 6,015, 710, 5,986,053, 5,977,296, 5,902,786, 5,864,010, 5,786,461, 5,773,571, 5,766,855, 5,736,336, 5,719,262, and 5,714,331).

Oligonucleotides may also include species that include at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)_nNH_2$ or $O(CH_2)_nCH_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of EIF4A to inhibit the function of that RNA.

The oligonucleotides in accordance with certain embodiments of this invention comprise from about 3 to about 50 subunits. It is more preferred that such oligonucleotides and analogs comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention can be conveniently and routinely made through the well-known technique of solid phase synthesis. Equipment for such syntheses is sold by several vendors (e.g. Applied Biosystems). Any other means for such synthesis may also be employed; however, the actual synthesis of the oligonucleotides is well within the talents of those of skill in the art. Methods of preparing other oligonucleotides such as phosphorothioates and alkylated derivatives are also well known to those of skill in the art.

Ribozymes.

In another approach, eIF4A expression can be inhibited by the use of ribozymes. As used herein, "ribozymes" include RNA molecules that contain antisense sequences for specific recognition, and an RNA-cleaving enzymatic activity. The catalytic strand cleaves a specific site in a target (eIF4A) RNA, preferably at greater than stoichiometric concentration. Two "types" of ribozymes are particularly useful in this invention, the hammerhead ribozyme (Rossi et al. (1991) *Pharmac. Ther.* 50: 245-254) and the hairpin ribozyme (Hampel et al. (1990) *Nucl. Acids Res.* 18: 299-304, and U.S. Pat. No. 5,254,678).

Because both hammerhead and hairpin ribozymes are catalytic molecules having antisense and endoribonucleotidase activity, ribozyme technology has emerged as a potentially powerful extension of the antisense approach to gene inactivation. The ribozymes of the invention typically consist of RNA, but such ribozymes may also be composed of nucleic acid molecules comprising chimeric nucleic acid sequences (such as DNA/RNA sequences) and/or nucleic acid analogs (e.g., phosphorothioates).

Accordingly, within one aspect of the present invention ribozymes have the ability to inhibit eIF4A expression. Such ribozymes may be in the form of a "hammerhead" (for example, as described by Forster and Symons (1987) *Cell* 48: 211-220; Haseloff and Gerlach (1988) *Nature* 328: 596-600; Walbot and Bruening (1988) *Nature* 334: 196; Haseloff and Gerlach (1988) *Nature* 334: 585) or a "hairpin" (see, e.g. U.S. Pat. No. 5,254,678 and Hampel et al., European Patent Publication No. 0 360 257, published Mar. 26, 1990), and have the ability to specifically target, cleave and eIF4A nucleic acids.

Ribozymes, as well as DNA encoding such ribozymes and other suitable nucleic acid molecules can be chemically synthesized using methods well known in the art for the synthesis of nucleic acid molecules. Alternatively, Promega, Madison, Wis., USA, provides a series of protocols suitable for the production of RNA molecules such as ribozymes. The ribozymes also can be prepared from a DNA molecule or other nucleic acid molecule (which, upon transcription, yields an RNA molecule) operably linked to an RNA polymerase promoter, e.g., the promoter for T7 RNA polymerase or SP6 RNA polymerase. Such a construct may be referred to as a vector. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitor upon incubation with the RNA polymerase and appropriate nucleotides. In a separate embodiment, the DNA may be inserted into an expression cassette (see, e.g., Cotten and Birnstiel (1989) *EMBO J.* 8(12):3861-3866; Hempel et al. (1989) *Biochem.* 28: 4929-4933, etc.).

After synthesis, the ribozyme can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

The ribozyme molecule also can be in a host prokaryotic or eukaryotic cell in culture or in the cells of an organism/patient. Appropriate prokaryotic and eukaryotic cells can be transfected with an appropriate transfer vector containing the DNA molecule encoding a ribozyme of this invention. Alternatively, the ribozyme molecule, including nucleic acid molecules encoding the ribozyme, may be introduced into the host cell using traditional methods such as transformation using calcium phosphate precipitation (Dubensky et al. (1984) *Proc. Natl. Acad. Sci., USA,* 81: 7529-7533), direct microinjection of such nucleic acid molecules into intact target cells (Acsadi et al. (1991) *Nature* 352: 815-818), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al. (1990) *Proc. Natl. Acad. Sci., USA,* 89:6094), lipofection (Felgner et al. (1989) *Proc. Natl. Acad. Sci. USA* 84: 7413-7417), microprojectile bombardment (Williams et al. (1991) *Proc. Natl. Acad. Sci., USA,* 88: 2726-2730), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., (1985) *Pharmac. Ther.* 29: 69; and Friedmann et al. (1989) *Science* 244: 1275), and DNA ligand (Wu et al (1989) *J. Biol. Chem.* 264: 16985-16987), as well as psoralen inactivated viruses such as Sendai or Adenovirus. In one preferred embodiment, the ribozyme is introduced into the host cell utilizing a lipid, a liposome or a retroviral vector.

When the DNA molecule is operatively linked to a promoter for RNA transcription, the RNA can be produced in the host cell when the host cell is grown under suitable conditions favoring transcription of the DNA molecule. The vector can be, but is not limited to, a plasmid, a virus, a retrotransposon or a cosmid. Examples of such vectors are disclosed in U.S. Pat. No. 5,166,320. Other representative vectors include, but are not limited to adenoviral vectors (e.g., WO 94/26914, WO 93/9191; Kolls et al. (1994) PNAS 91(1):215-219; Kass-Eisler et al., (1993) *Proc. Natl. Acad. Sci., USA,* 90(24): 11498-502, Guzman et al. (1993) *Circulation* 88(6): 2838-48, 1993; Guzman et al. (1993) *Cir. Res.* 73(6):1202-1207, 1993; Zabner et al. (1993) *Cell* 75(2): 207-216; Li et al. (1993) *Hum Gene Ther.* 4(4): 403-409; Caillaud et al. (1993) *Eur. J Neurosci.* 5(10): 1287-1291), adeno-associated vector type 1 ("AAV-1") or adeno-associated vector type 2 ("AAV-2") (see WO 95/13365; Flotte et al. (1993) *Proc. Natl. Acad. Sci., USA,* 90(22):10613-10617), retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218) and herpes viral vectors (e.g., U.S. Pat. No. 5,288,641). Methods of utilizing such vectors in gene therapy are well known in the art, see, for example, Larrick and Burck (1991) *Gene Therapy: Application of Molecular Biology,* Elsevier Science Publishing Co., Inc., New York, N.Y., and Kreigler (1990) *Gene Transfer and Expression: A Laboratory Manual,* W.H. Freeman and Company, New York.

To produce ribozymes in vivo utilizing vectors, the nucleotide sequences coding for ribozymes are preferably placed under the control of a strong promoter such as the lac, SV40 late, SV40 early, or lambda promoters. Ribozymes are then produced directly from the transfer vector in vivo RNAi Inhibition of eIF4A.

Post-transcriptional gene silencing (PTGS) or RNA interference (RNAi) refers to a mechanism by which double-stranded (sense strand) RNA (dsRNA) specifically blocks expression of its homologous gene when injected, or otherwise introduced into cells. The discovery of this incidence came with the observation that injection of antisense or sense RNA strands into *Caenorhabditis elegans* cells resulted in gene-specific inactivation (Guo and Kempheus (1995) *Cell* 81: 611-620). While gene inactivation by the antisense strand was expected, gene silencing by the sense strand came as a surprise. Adding to the surprise was the finding that this gene-specific inactivation actually came from trace amounts of contaminating dsRNA (Fire et al. (1998) *Nature* 391: 806-811).

Since then, this mode of post-transcriptional gene silencing has been tied to a wide variety of organisms: plants, flies, trypanosomes, planaria, hydra, zebrafish, and mice (Zamore et al. (2000). *Cell* 101: 25-33; Gura (2000) *Nature* 404: 804-808). RNAi activity has been associated with functions as disparate as transposon-silencing, anti-viral defense mechanisms, and gene regulation (Grant (1999) *Cell* 96: 303-306).

By injecting dsRNA into tissues, one can inactivate specific genes not only in those tissues, but also during various stages of development. This is in contrast to tissue-specific knockouts or tissue-specific dominant-negative gene expressions, which do not allow for gene silencing during various stages of the developmental process (see, e.g., Gura (2000) *Nature* 404: 804-808). The double-stranded RNA is cut by a nuclease activity into 21-23 nucleotide fragments. These fragments, in turn, target the homologous region of their corresponding mRNA, hybridize, and result in a double-stranded substrate for a nuclease that degrades it into fragments of the same size (Hammond et al. (2000) *Nature,* 404: 293-298; Zamore et al. (2000). *Cell* 101: 25-33).

It has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) *EMBO J.,* 21(21): 5864-5874; Tabara et al. (2002) *Cell* 109 (7):861-71; Martinez et al. (2002) *Cell* 110(5): 563; Hutvagner and Zamore (2002), *Science* 297: 2056, and the like.

Using the known nucleotide sequence for the EIF4A gene and/or mRNA, EIF4A siRNAs can readily be produced. In various embodiments siRNA that inhibit EIF4A can comprise partially purified RNA, substantially pure RNA, synthetic RNA, recombinantly produced RNA, as well as altered RNA that differs from naturally-occurring RNA by the addition, deletion, substitution and/or alteration of one or more nucleotides. Such alterations can include, for example, addition of non-nucleotide material, such as to the end(s) of the siRNA or to one or more internal nucleotides of the siRNA, including modifications that make the siRNA resistant to nuclease digestion.

In various embodiments one or both strands of the siRNA can comprise a 3' overhang. As used herein, a "3' overhang" refers to at least one unpaired nucleotide extending from the 3'-end of an RNA strand. Thus in one embodiment, the siRNA comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length.

In an illustrative embodiment in which both strands of the siRNA molecule comprise a 3' overhang, the length of the overhangs can be the same or different for each strand. In certain embodiments the 3' overhang is present on both strands of the siRNA, and is one, two, or three nucleotides in length. For example, each strand of the siRNA can comprise 3' overhangs of dithymidylic acid ("TT") or diuridylic acid ("uu").

In order to enhance the stability of the siRNA, the 3' overhangs can be also stabilized against degradation. In one embodiment, the overhangs are stabilized by including purine nucleotides, such as adenosine or guanosine nucleotides. In certain embodiments substitution of pyrimidine nucleotides by modified analogues, e.g., substitution of uridine nucleotides in the 3' overhangs with 2'-deoxythymidine, is tolerated and does not affect the efficiency of RNAi degradation. In particular, it is believed the absence of a 2' hydroxyl in the 2'-deoxythymidine can significantly enhance the nuclease resistance of the 3' overhang In certain embodiments, the siRNA comprises the sequence AA(N19)TT (SEQ ID NO:1), AA(N21)TT (SEQ ID NO:2), NA(N21) (SEQ ID NO:3), and the like, where N is any nucleotide. In various embodiments these siRNA comprise approximately 30%-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another illustrative embodiment, the siRNA comprises the sequence NAR(N17)YNN (SEQ ID NO:4), where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In various embodiments the siRNA of the invention can be targeted to any stretch of approximately 10-30, or 15-25, or 19-25 contiguous nucleotides in any of the target mRNA sequences (the "target sequence"). Techniques for selecting target sequences for siRNA are given, for example, in Tuschl et al., "The siRNA User Guide," revised May 6, 2004. The "siRNA User Guide" is available on the world wide web at a website maintained by Dr. Thomas Tuschl, and can be found by accessing the website of Rockefeller University and searching with the keyword "siRNA." In addition, the "siRNA User Guide" can be located by performing a google search for "siRNA User Guide" and can also be found at "www.rockefeller.edu/labheads/tuschl/sirna.html. Techniques for selecting target sequences for siRNA and miRNA can also be found in Sioud (2008) *siRNA and miRNA Gene Silencing: From Bench to Bedside (Methods in Molecular Biology)*, Humana Press.

In certain embodiments the sense strand of the present siRNA comprises a nucleotide sequence identical to any contiguous stretch of about 19 to about 25 nucleotides in the target eukaryotic initiation factor 4A (EIF4A) mRNA. Generally, a target sequence on the target mRNA can be selected from a given cDNA sequence corresponding to the target mRNA, preferably beginning 50 to 100 nucleotides downstream (i.e., in the 3' direction) from the start codon. The target sequence can, however, be located in the 5' or 3' untranslated regions, or in the region nearby the start.

The EIF4A silencing siRNAs can be obtained using a number of techniques known to those of skill in the art. For example, the siRNA can be chemically synthesized or recombinantly produced using methods known in the art, such as the *Drosophila* in vitor system described in U.S. published application US 2002/0086356.

In certain embodiments the siRNAs are chemically synthesized using appropriately protected ribonucleoside phosphoramidites and a conventional DNA/RNA synthesizer. The siRNAs can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Custom siRNA can be obtained from commercial suppliers (see, e.g., Thermo Fisher Scientific, Lafayette Colo.; Qiagen, Valencia, Calif.; Applied Biosystems, Foster City, Calif.; and the like).

In certain embodiments siRNA can also be expressed from recombinant circular or linear DNA plasmids using any suitable promoter. Suitable promoters for expressing siRNA from a plasmid include, for example, the U6 or H1 RNA pol III promoter sequences and the cytomegalovirus promoter. Selection of other suitable promoters is within the skill in the art. The recombinant plasmids can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the target area(s) in vivo. The use of recombinant plasmids to deliver siRNA to cells in vivo is discussed in more detail below.

siRNA can be expressed from a recombinant plasmid either as two separate, complementary RNA molecules, or as a single RNA molecule with two complementary regions. Selection of plasmids suitable for expressing siRNAs, methods for inserting nucleic acid sequences for expressing the siRNA into the plasmid, and methods of delivering the recombinant plasmid to the cells of interest are within the skill in the art (see, e.g., Tuschl (2002) *Nat. Biotechnol.*, 20: 446-448; Brummelkamp et al. (2002) *Science* 296: 550 553; Miyagishi et al. (2002) *Nat. Biotechnol.* 20: 497-500; Paddison et al. (2002) *Genes Dev.* 16: 948-958; Lee et al. (2002) *Nat. Biotechnol.* 20: 500-505; Paul et al. (2002) *Nat. Biotechnol.* 20: 505-508, and the like).

In one illustrative embodiment, a plasmid comprising nucleic acid sequences for expressing an siRNA for inhibiting EIF4A comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid is ultimately intended for use in producing an recombinant adeno-associated viral vector comprising the same nucleic acid sequences for expressing the siRNA As used herein, "in operable connection with a polyT termination sequence" means that the nucleic acid sequences encoding the sense or antisense strands are adjacent to the polyT termination signal in the 5' direction or sufficiently close so that during transcription of the sense or antisense sequences from the plasmid, the polyT termination signals act to terminate transcription after the desired product is transcribed.

As used herein, "under the control" of a promoter means that the nucleic acid sequences encoding the sense or antisense strands are located 3' of the promoter, so that the promoter can initiate transcription of the sense or antisense coding sequences.

In various embodiments the siRNA can be expressed from recombinant viral vectors intracellularly at or near the target site(s) in vivo. The recombinant viral vectors comprise sequences encoding the siRNA of the invention and any suitable promoter for expressing the siRNA sequences. Suitable promoters include, but are not limited to, the U6 or H1 RNA pol III promoter sequences and the cytomegalovirus promoter. Selection of other suitable promoters is within the skill in the art. The recombinant viral vectors can also comprise inducible or regulatable promoters for expression of the siRNA in a particular tissue or in a particular intracellular environment. The use of recombinant viral vectors to deliver siRNA of the invention to cells in vivo is discussed in more detail below.

The siRNA can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector can be pseudotyped with surface proteins from vesicular stomatitis virus (VSV), rabies, Ebola, Mokola, and the like.

Selection of recombinant viral vectors suitable for use in methods for inserting nucleic acid sequences for expressing the siRNA into the vector, and methods of delivering the viral vector to the cells of interest are within the skill in the art (see, e.g., Domburg (1995) *Gene Therap.* 2: 301-310; Eglitis (1988) *Biotechniques* 6: 608-614; Miller (1990) *Hum. Gene Therap.* 1: 5-14; Anderson (1998) *Nature* 392: 25-30, and the like).

In certain embodiments suitable viral vectors include those derived from AV and AAV. In one illustrative embodiment, the siRNA of the invention is expressed as two separate, complementary single-stranded RNA molecules from a recombinant AAV vector comprising, for example, either the U6 or H1 RNA promoters, or the cytomegalovirus (CMV) promoter. A suitable AV vector for expressing the siRNA, a method for constructing the recombinant AV vector, and a method for delivering the vector into target cells, are described in Xia et al. (2002) *Nat. Biotech.* 20: 1006 1010.

Suitable AAV vectors for expressing the siRNA, methods for constructing the recombinant AV vector, and methods for delivering the vectors into target cells are also described in Samulski et al. (1987) *J. Virol.* 61: 3096-3101; Fisher et al. (1996) *J. Virol.*, 70: 520-532; Samulski et al. (1989) *J. Virol.* 63: 3822-3826; U.S. Pat. Nos. 5,252,479 and 5,139,941; International Patent Application Nos. WO 1994/013788; and WO 1993/024641, and the like.

The ability of an siRNA containing a given target sequence to cause RNAi-mediated degradation of the target mRNA can be evaluated using standard techniques for measuring the levels of RNA or protein in cells. For example, siRNA can be delivered to cultured cells, and the levels of target mRNA can be measured by Northern blot or dot blotting techniques, or by quantitative RT-PCR. Alternatively, the levels of EIF4A in cells can be measured by ELISA or Western blot.

RNAi-mediated degradation of target EIF4A mRNA by an siRNA containing a given target sequence can also be evaluated with suitable animal models of aging.

In certain embodiments the siRNA can be delivered as a small hairpin RNA or short hairpin RNA (shRNA). shRNA is a sequence of RNA that makes a tight hairpin turn that can be used to silence gene expression via RNA interference. In typical embodiments, shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it.

The shRNA/siRNA described herein target and cause the RNAi-mediated degradation of EIF4A, or alternative splice forms, mutants or cognates thereof. Degradation of the target mRNA by the present siRNA reduces the production of a functional gene product from the EIF4A gene. Thus, methods are provided for inhibiting expression of EIF4A in a subject, comprising administering an effective amount of an EIF4A siRNA to the subject, such that the target mRNA is degraded.

It is understood that the siRNA of described herein can degrade the target mRNA in substoichiometric amounts. Without wishing to be bound by any theory, it is believed that the siRNA described herein cause degradation of the target mRNA in a catalytic manner. Thus, compared to standard anti-angiogenic therapies, significantly less siRNA needs to be delivered to have a therapeutic effect.

One skilled in the art can readily determine an effective amount of the siRNA of the invention to be administered to a given subject, by taking into account factors such as the size and weight of the subject; the age, health and sex of the subject; the route of administration; and whether the administration is regional or systemic.

RNA aptamers to Inhibit EIF4A

In certain embodiments RNA aptamers can be used to inhibit EIF4A. Oguro et al. (2003) RNA 9: 394-407 generated RNA aptamers with high affinity for eIF4A by in vitor RNA selection-amplification. On binding, the RNAs inhibited ATP hydrolysis. One class of RNAs contained members that exhibit dissociation constant of 27 nM for eIF4A and severely inhibit cap-dependent in vitor translation. The binding affinity was increased on Arg substitution in the conserved motif Ia of eIF4A, which was believed to improve a predicted arginine network to bind RNA substrates. It is believed that the selected RNAs interact cooperatively with both domains of eIF4A, either in the dumbbell or the compact form, and entrap it into a dead-end conformation, probably by blocking the conformational change of eIF4A.

Illustrative aptamers are shown in Table 1.

TABLE 1

Illustrative aptamers for inhibiting EIF4A based on FIG. 1 in Oguro et al. supra.

| | Aptamer | SEQ ID NO |
|---|---|---|
| 1 | ------CAGGCGUUUAGCCUCUAAGUA-----ACAGGGGGCUCCCAUGAGC------- | 5 |
| 2 | AUUGAAGUAGCGUUUAGGUUUAGAG---------CCGACCCUCCCAAA--------- | 6 |
| 3 | ---------AAGUUUAGUCAGACACA----AACAACUGACCUCCCCGCGAGC------ | 7 |
| 4 | ------AUAAGGUUUAGCCACACG--------CTCGUGGCCUCCCCAAUGGGUC---- | 8 |
| 5 | -----------GUUUAGCGGUGGAUGGGCAAAGCUACCGCCUCCAGAGCU------- | 9 |
| 6 | -------GAGCGUUUAGGCACACA----------CCUGCCCUCCCACUACACGAGCA- | 10 |
| 7 | -------AAGAGUUUAGGUGUCGGG---------CCACACCCUCCCAUUUAUCAAA--- | 11 |
| 8 | ---------AGGUUUAGGCCCAUACA-----ACCUGGGCCCUCCCAAGACCUUC---- | 12 |
| 9 | -----UAAGAGCUUUAGUUGCGAU-------GUGCGCAACCUCCCCUGAGCC------ | 13 |
| 10 | -----CAAAGCGAUUAGGUCCGA----------GAGGUCCCUCCCAGCCUCGCGC--- | 14 |
| 11 | ----------------ACAUUGCAUCGACAGCUGCAAGGCUCCCGCCGUACAAACC | 15 |
| 12 | ---------------ACAGUACUUAACCACAAGCAGUACGGCUCCCAGCUGAGAG---- | 16 |
| 13 | ------------ACAGGUUGUUAGACAAGUAGCCAACCGGCUCCCGCCGACC------ | 17 |
| 14 | ----------------ACAUUGCAUCGACAGCUGCAAGGCUCCCGCCGUACAAACC- | 18 |
| 15 | ----------------AUAUAGCAUUAAAGUUGCUAAGCUCCCAAGUAACCUCUAC | 19 |
| 16 | ---------------ACAGCAAGUACCAUGAAGCCUUGCGGCUCCCAUGAACCCC---- | 20 |
| 17 | ----------------AGACCGACACAAAAGCGUCGGCGCUCCCUAGUAAUGAAGC- | 21 |
| 18 | ----------------AGACCGACAUAGAAGCGUCGGCGCUCCCUAGUAAUGAAGC- | 22 |
| 19 | ----------------AGACCGACAUAAAAGCGUCGGCGCUCCCUAGUAAUGUAGC- | 23 |
| 20 | GGGGACCGCGCCCCACAUGUGAGUGAGGCCGAAACGUAGA | 24 |
| 21 | GGGGACCGCGCCCCACAUGUGAGUGAGGCCGAAACAUAGA | 25 |
| 22 | GGGGACCGCGCCCCACAUGUGAGUGAGACCGAAACGUAGA | 26 |
| 23 | GGGGACCGCGCCCCACAUGUGAGUGAGACCGAAGCGUAGA | 27 |
| 24 | GGGGAUCGCGCCCCACAUGUGAGUGAGGCCGAAACGUAGA | 28 |
| 25 | GGGGACCGCGCCCCACACGUGAGUGAGGCCGAAACGUAGA | 29 |
| 26 | GGGGACCGCGCCCCACAUGUGAGUGAGGCCGAAACGUAGG | 30 |
| 27 | GGGGACCGCGCCCCACAUGUGAGUGAGGUCGAAACGUAGA | 31 |
| 28 | GGGGACCGCGCCCCACAUGUGAGUGAGGCCGAAACAUAGA | 32 |
| 29 | GGGGACCGCGCCCCACGUGUGAGUGAGGCCGAAACGUAGA | 33 |
| 30 | UGUGGAUGAUUUGUAUGAUCGCGCAUACAA | 34 |
| 31 | UGUGGAUGAUCUGUAUGAUCGCGCAUACAG | 35 |
| 32 | UGUGGAUGAUUUGUAUGAUCGCGCAUACAG | 36 |
| 33 | UGUGGAUGGUCUGUAUGAUCGCGCAUACAG | 37 |
| 34 | UGUGGAUGAAUGUGUAGAUCGCGCUACGCA | 38 |
| 35 | UGUGGAUGAACGCGUAGAUCGCGCUACGCU | 39 |

II. Pharmaceutical Formulations and Administration.

In order to carry out certain methods described herein, one or more active agents (e.g., eIF4A inhibitors) are administered to a mammal in need thereof, e.g., as a geroprotector that can be used for slowing aging, prolonging lifespan of an individual or cells in an individual, and/or improving quality of life of an individual developing or having a risk of developing age-associated manifestations and/or pathologies.

The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, acid salts of the active agents can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

An acid addition salt can be reconverted to the free base by treatment with a suitable base. Certain typical acid addition salts of the active agents described herein include, for example, halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Certain typical basic salts include, but are not limited to, alkali metal salts, e.g., the sodium salt, and copper salts.

Preparation of esters typically involves functionalization of, e.g, HYDROXYL and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein are useful for parenteral, topical, oral, nasal (or otherwise inhaled), rectal, or local administration, such as by aerosol or transdermally, prophylactically and/or therapeutically (e.g., as a geroprotector that can be used for slowing aging, prolonging lifespan of an individual or cells in an individual, and/or improving quality of life of an individual The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The active agents described herein can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components and the resulting composition is compressed. Where necessary the compressed product is coated, e.g., known methods for masking the taste or for enteric dissolution or sustained release. Suitable coating materials include, but are not limited to ethylcellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In therapeutic or prophylactic applications, the compositions of this invention are administered to a mammal (e.g., to a human, an elderly human, etc.) as a geroprotector that can be used for slowing aging, prolonging lifespan of an individual or cells in an individual, and/or improving quality of life of an individual developing or having a risk of developing age-associated manifestations and/or pathologies in an amount sufficient inhibit aging (e.g., to reduce or eliminate the severity, progression or onset of one or more symptoms of aging). An amount adequate to accomplish this is defined as a "therapeutically effective dose." Amounts effective for this use will depend upon the age of the subject, the severity of the age-associated symptoms, and the general state of the subject's health. Single or multiple administrations of the compositions may be administered depending on the dosage and frequency as required and tolerated by the subject. In any event, the composition should provide a sufficient quantity of the active agents of the formulations of this invention to effectively treat (ameliorate one or more symptoms in) the subject.

The concentration of active agent(s) can vary widely, and will typically be selected primarily based on activity of the active ingredient(s), body weight and the like in accordance with the particular mode of administration selected and the subject's needs (see, e.g., Remington's Pharmaceutical Science, 15th ed., Mack Publishing Company, Easton, Pa. (1980), Remington: The Science and Practice of Pharmacy, 21st Ed. 2005, Lippincott Williams & Wilkins, and the like). In certain embodiments amounts, however, will typically be selected to provide dosages ranging from about 0.001, 0.01, 0.1 1, or 10 mg/kg/day to about 50 mg/kg/day and sometimes higher. In certain embodiments typical dosages range from about 1 mg/kg/day to about 3 mg/kg/day, preferably from about 3 mg/kg/day to about 10 mg/kg/day, more preferably from about 10 mg/kg/day to about 20.0 mg/kg/day, and most preferably from about 20 mg/kg/day to about 50 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic and/or prophylactic regimen in a particular subject or group of subjects.

In certain embodiments, the active agents of this invention are administered to the oral cavity. This is readily accomplished by the use of lozenges, aerosol sprays, mouthwash, coated swabs, and the like.

In certain embodiments the active agents of this invention are administered systemically (e.g., orally, or as an injectable) in accordance with standard methods well known to those of skill in the art. In certain embodiments, the agents, can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other formulations for topical delivery include, but are not limited to, ointments, gels, sprays, fluids, and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

As indicated above, various buccal, and sublingual formulations are also contemplated.

In certain embodiments, one or more active agents of the present invention can be provided as a "concentrate", e.g., in a storage container (e.g., in a premeasured volume) ready for dilution, or in a soluble capsule ready for addition to a volume of water, alcohol, hydrogen peroxide, or other diluent.

While the invention is described with respect to use in humans, it is also suitable for animal, e.g., veterinary use. Thus certain preferred organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Formulation and Administration of siRNA or Other Nucleic Acid Based Active Agents)

Suitable delivery reagents for administration in conjunction with the siRNA (or other nucleic acid based active agents) include, but are not limited to, the Minis Transit TKO lipophilic reagent; lipofectin; lipofectamine; cellfectin; or polycations (e.g., polylysine), or liposomes. One illustrative delivery reagent is a liposome.

Liposomes can aid in the delivery of the siRNA (or other vectors or nucleic acids) to a particular tissue and can also increase the blood half-life of the siRNA. Liposomes suitable for use include those formed from standard vesicle-forming lipids, that generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, and the like.

In certain embodiments the liposomes encapsulating the present siRNA (or other vector and/or nucleic acid) comprises a ligand molecule that can target the liposome to a particular cell or tissue of interest.

In certain embodiments the liposomes encapsulating the present siRNA (or other vector and/or nucleic acid) are modified so as to avoid clearance by the mononuclear macrophage and reticuloendothelial systems, for example by having opsonization-inhibition moieties bound to the surface of the structure. In one embodiment, a liposome can comprise both opsonization-inhibition moieties and a ligand.

Opsonization-inhibiting moieties for use in preparing the liposomes are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the macrophage-monocyte system ("MMS") and reticuloendothelial system ("RES"); e.g., as described in U.S. Pat. No. 4,920,016. Liposomes modified with opsonization-inhibition moieties thus remain in the circulation much longer than unmodified liposomes. For this reason, such liposomes are sometimes called "stealth" liposomes.

Opsonization inhibiting moieties suitable for modifying liposomes include water-soluble polymers with a molecular weight from about 500 to about 40,000 daltons, or from about 2,000 to about 20,000 daltons. Such polymers include, but are not limited to polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

In certain embodiments the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids that express siRNA (or other vector and/or nucleic acid) can also be administered directly or in conjunction with a suitable delivery reagent, including the Minis Transit LT1 lipophilic reagent; lipofectin; lipofectamine; cellfectin; polycations (e.g., polylysine) or liposomes The siRNA of the invention can be administered to the subject by any means suitable for delivering the siRNA (or other vector and/or nucleic acid) to the cells of the subject. For example, the siRNA can be administered by gene gun, electroporation, or by other suitable parenteral or enteral administration routes. Suitable enteral administration routes include oral, rectal, or intranasal delivery. Suitable parenteral administration routes include intravascular administration (e.g. intravenous bolus injection, intravenous infusion, intra-arterial bolus injection, intra-arterial infusion and catheter instillation into the vasculature); peri- and intra-tissue injection; subcutaneous injection or deposition including subcutaneous infusion (such as by osmotic pumps); direct application for example by a catheter or other placement device (e.g., a retinal pellet or a suppository or an implant comprising a porous, non-porous, or gelatinous material); and inhalation.

The siRNA (or other vector and/or nucleic acid) of the invention can be administered in a single dose or in multiple doses. Where the administration of the siRNA (or other vector and/or nucleic acid) is by infusion, the infusion can be a single sustained dose or can be delivered by multiple infusions.

One skilled in the art can also readily determine an appropriate dosage regimen for administering the siRNA (or other vector and/or nucleic acid) to a given subject. For example, the siRNA can be administered to the subject once, for example as a single injection or deposition at or near the neovascularization site. Alternatively, the siRNA can be administered once or twice daily to a subject for a period of from about three to about twenty-eight days, more preferably from about seven to about ten days. Where a dosage regimen comprises multiple administrations, it is understood that the effective amount of siRNA administered to the subject can comprise the total amount of siRNA administered over the entire dosage regimen.

The siRNA (or other vector and/or nucleic acid) of the invention are preferably formulated as pharmaceutical compositions prior to administering to a subject, according to techniques known in the art (see, e.g., discussion above). In certain embodiments are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

III. Assays for Inhibitors of Eukaryotic Initiation Factor 4A (EIF4A)

As indicated above, in one aspect, this invention pertains to the discovery that inhibition of eIF4A inhibits aging process(es). EIF4A thus provides a target to screen for inhibitors of the aging process. In various embodiments the methods can involve contacting a cell, a tissue, an organism with one or more test agents and detecting (resulting changes in) the expression level and/or activity level of eIF4A and/or a measure/marker of an aging process.

It is noted that when screening for eIF4A inhibitors, a positive assay result need not indicate the particular test agent is a good pharmaceutical. Rather a positive result can simply indicate that the test agent can be used to inhibit eIF4A activity and/or can also serve as a lead compound in the development of other modulators.

Using the methods described herein, test agents can readily be screened for the ability to inhibit eIF4A expression and/or activity.

Activity-Based Assays.

For example, inhibition of eIF4A expression and/or activity can readily be determined by placing one or more reporter genes under control of a promoter system whose regulation is controlled by eIF4A. Cell(s) containing such constructs are contacted with test agents, and a reduction in the reporter indicates that the test agent(s) inhibit eIF4A expression or activity.

Figure 3A:
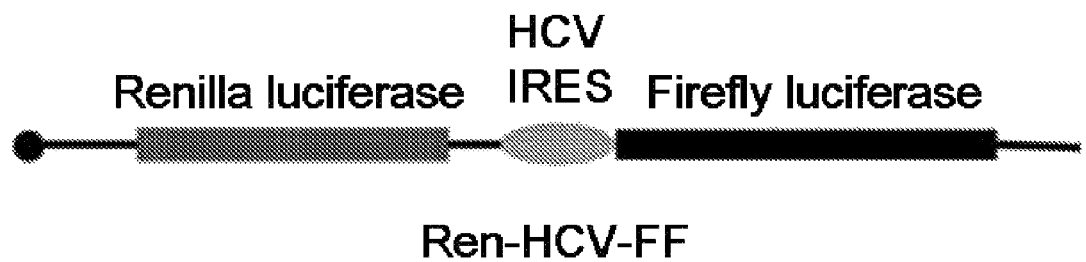
FIGS. 3A and 3B show that resveratrol inhibits eIF4A-dependent translation initiation.
Figure 3B:
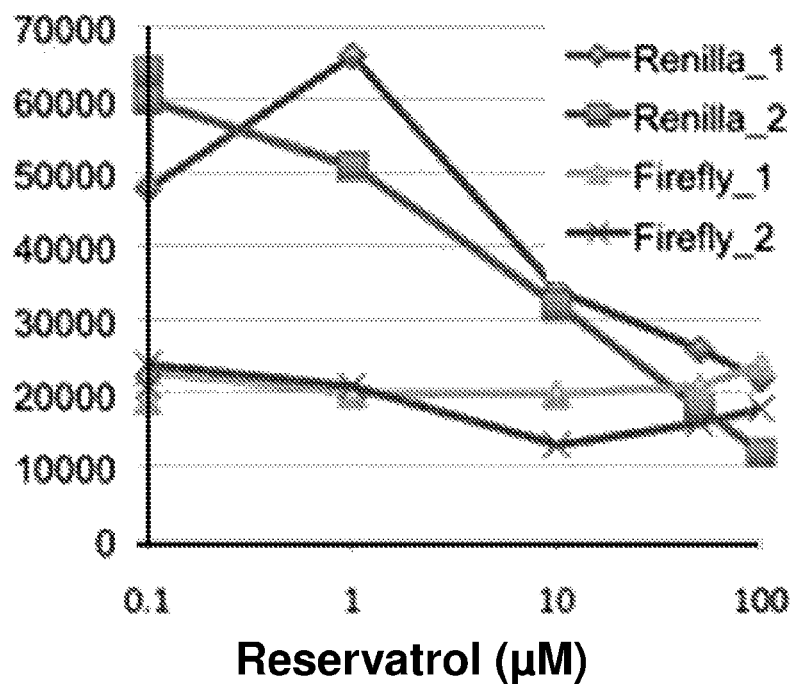

One such illustrative assay is shown in Example 1. In this example, a standard bicistronic dual-luciferase mRNA reporter pcDNA/Ren/HCV/FF (Bordeleau et al. (2006) *Nat. Chem. Biol.*, 2: 213-220) where translation of *Renilla* luciferase is cap-dependent (i.e., eIF4A-requiring), and translation of firefly luciferase is mediated by the HCV IRES which does not require eIF4A (FIG. 3A) is used. As shown in FIG. 3B, expression of *Renilla* luciferase was inhibited in a dose-dependent manner by the eIF4A inhibitor resveratrol, but expression of firefly luciferase was unaffected.

Nucleic-Acid Based Assays.

Using the known nucleic acid sequences for eIF4A, copy number and/or, eIF4A expression level, can be directly measured according to a number of different methods as described below. In particular, expression levels of a gene can be altered by changes in the copy number of the gene, and/or by changes in the transcription of the gene product (i.e. transcription of mRNA), and/or by changes in translation of the gene product (i.e. translation of the protein), and/or by post-translational modification(s) (e.g. protein folding, glycosylation, etc.). Thus useful assays of this invention include assaying for copy number, level of transcribed mRNA, level of translated protein, activity of translated protein, etc. Examples of such approaches are described below.

1) Target Molecules.

Changes in expression level can be detected by measuring changes in mRNA and/or a nucleic acid derived from the mRNA (e.g. reverse-transcribed cDNA, etc.). In order to measure the eIF4A expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism, or from cells in culture. The sample may be of any biological tissue or fluid. Biological samples may also include organs or sections of tissues such as frozen sections taken for histological purposes.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

In a certain embodiments, the "total" nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1-3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to assaying for expression level. Methods of amplifying nucleic acids are well known to those of skill in the art and include, but are not limited to polymerase chain reaction (PCR, see. e.g, Innis, et al., (1990) *PCR Protocols. A guide to Methods and Application*. Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In one illustrative embodiment, where it is desired to quantify the transcription level (and thereby expression) of eIF4A in a sample, the nucleic acid sample is one in which the concentration of the eIF4A mRNA transcript(s), or the concentration of the nucleic acids derived from the eIF4A mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In one simple embodiment, the eIF4A-containing nucleic acid sample is the total mRNA or a total cDNA isolated and/or otherwise derived from a biological sample. The nucleic acid may be isolated from the sample according to any of a number of methods well known to those of skill in the art as indicated above.

2) Hybridization-Based Assays.

Using known eIFrA sequences detecting and/or quantifying the eIF4A transcript(s) can be routinely accomplished using nucleic acid hybridization techniques (see, e.g., Sambrook et al. *supra*). For example, one method for evaluating the presence, absence, or quantity of eIF4A reverse-transcribed cDNA involves a "Southern Blot". In a Southern Blot, the DNA (e.g., reverse-transcribed eIF4A mRNA), typically fragmented and separated on an electrophoretic gel, is hybridized to a probe specific for eIF4A (or to a mutant thereof). Comparison of the intensity of the hybridization signal from the eIF4A probe with a "control" probe (e.g. a probe for a "housekeeping gene) provides an estimate of the relative expression level of the target nucleic acid.

Alternatively, the eIF4A mRNA can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target eIF4A mRNA. Appropriate controls (e.g. probes to housekeeping genes) provide a reference for evaluating relative expression level.

An alternative means for determining the eIF4A expression level is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-Based Assays.

In another embodiment, amplification-based assays can be used to measure eIF4A expression (transcription) level. In such amplification-based assays, the target nucleic acid sequences (i.e., eIF4A) act as template(s) in amplification reaction(s) (e.g. Polymerase Chain Reaction (PCR) or reverse-transcription PCR(RT-PCR)). In a quantitative amplification, the amount of amplification product will be proportional to the amount of template (e.g., eIF4A mRNA) in the original sample. Comparison to appropriate (e.g. healthy tissue or cells unexposed to the test agent) controls provides a measure of the eIF4A transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

One typical internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of labeled nucleic acid (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al. (1990) Academic Press, Inc. N.Y. The known nucleic acid sequence(s) for EIF4A are sufficient to enable one of skill to routinely select primers to amplify any portion of the gene.

4) Hybridization Formats and Optimization of Hybridization Conditions.

a) Array-Based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a certain embodiments, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high-density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high-density arrays is also described in U.S. Pat. Nos. 5,744, 305, 5,800,992 and 5,445,934.

b) Other Hybridization Formats.

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization.

Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like. Other labels include ligands that bind to labeled antibodies, fluorophores, chemi-luminescent agents, enzymes, and antibodies that can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

c) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.).

Methods of optimizing hybridization conditions are well known to those of skill in the art (see, e.g., Tijssen (1993) *Laboratory Techniques in Biochemistry and Molecular Biology*, Vol. 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105-114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

d) Labeling and Detection of Nucleic Acids.

The probes used herein for detection of eIF4A expression levels can be full length or less than the full length of the eIF4A or mutants thereof. Shorter probes are empirically tested for specificity. Preferred probes are sufficiently long so as to specifically hybridize with the eIF4A target nucleic acid(s) under stringent conditions. The preferred size range is from about 10, 15, or 20 bases to the length of the eIF4A mRNA, more preferably from about 30 bases to the length of the eIF4A mRNA, and most preferably from about 40 bases to the length of the eIF4A mRNA. The probes are typically labeled, with a detectable label as described above.

Polypeptide-Based Assays.

The effect of a test agent on EIF4A expression can also be determined by determining the effect of that test agent on translated eIF4A protein.

The polypeptide(s) encoded by the eIF4A gene can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, mass spectroscopy, and the like, or various immunological methods such as fluid or gel precipitin reactions, immunodiffusion (single or double), immunoelectrophoresis, radioimmunoas say (RIA), enzyme-linked immunosorbent assays (ELISAs), immunofluorescent assays, western blotting, and the like.

In one preferred embodiment, the eIF4A polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

In another preferred embodiment, Western blot (immunoblot) analysis is used to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target polypeptide(s) and may be directly labeled or alternatively may be subsequently detected using labeled antibodies (e.g., labeled sheep anti-mouse antibodies) that specifically bind to a domain of the antibody.

In preferred embodiments, the eIF4A polypeptide(s) are detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376,110; 4,517,288; and 4,837,168) are well suited to detection or quantification of the polypeptide(s) identified herein. For a review of the general immunoassays, see also Asai (1993) *Methods in Cell Biology Volume 37: Antibodies in Cell Biology*, Academic Press, Inc. New York; Stites & Ten (1991) *Basic and Clinical Immunology 7th Edition*.

Immunological binding assays (or immunoassays) typically utilize a "capture agent" to specifically bind to and often immobilize the analyte (eIF4A polypeptide). In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542).

Typical immunoassays for detecting the target polypeptide(s) are either competitive or noncompetitive.

Noncompetitive immunoassays are assays in which the amount of captured analyte is directly measured. In one "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (EIF4A polypeptide) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one embodiment, the antibody is immobilized on a solid substrate. The amount of target polypeptide bound to the antibody may be determined either by measuring the amount of target polypeptide present in an polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind eIF4A polypeptide(s), either alone or in combination. In the case where the antibody that binds eIF4A polypeptide is not labeled, a different detectable marker, for example, an enzyme-labeled antibody capable of binding to the monoclonal antibody which binds the eIF4A polypeptide, may be employed. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds eIF4A polypeptides is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein can be routinely produced or obtained commercially.

Assay Optimization.

The assays of this invention have immediate utility in screening for agents that inhibit eIF4A expression and/or activity in a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred PCR conditions), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration. Conversely, where it is desired to screen for modulators that alter transcription of eIF4A gene, nucleic acid based assays are preferred.

Routine selection and optimization of assay formats is well known to those of ordinary skill in the art.

Pre-Screening for Agents that Bind eIF4A.

In certain embodiments it is desired to pre-screen test agents for the ability to interact with (e.g. specifically bind to) an eIF4A (or mutant/allele) nucleic acid or polypeptide. Specifically, binding test agents are more likely to interact with and thereby modulate eIF4A expression and/or activity. Thus, in some embodiments, the test agent(s) are pre-screened for binding to eIF4A nucleic acids or to EIF4A proteins before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the eIF4A protein or nucleic acid is immobilized and exposed to a test agent (which can be labeled), or alternatively, the test agent(s) are immobilized and exposed to an eIF4A protein or to a eIF4A nucleic acid (which can be labeled). The immobilized moiety is then washed to remove any unbound material and the bound test agent or bound eIF4A nucleic acid or protein is detected (e.g. by detection of a label attached to the bound molecule). The amount of immobilized label is proportional to the degree of binding between the eIF4A protein or nucleic acid and the test agent.

Scoring the Assay(s).

The assays of this invention are scored according to standard methods well known to those of skill in the art. The assays of this invention are typically scored as positive where there is a difference between the activity seen with the test agent present or where the test agent has been previously applied, and the (usually negative) control. In preferred embodiments, the change is a statistically significant change, e.g. as determined using any statistical test suited for the data set provided (e.g. t-test, analysis of variance (ANOVA), semi-parametric techniques, non-parametric techniques (e.g. Wilcoxon Mann-Whitney Test, Wilcoxon Signed Ranks Test, Sign Test, Kruskal-Wallis Test, etc.). Preferably the statistically significant change is significant at least at the 85%, more preferably at least at the 90%, still more preferably at least at the 95%, and most preferably at least at the 98% or 99% confidence level). In certain embodiments, the change is at least a 10% change, preferably at least a 20% change, more preferably at least a 50% change and most preferably at least a 90% change.

Agents for Screening: Combinatorial Libraries (E.G., Small Organic Molecules)

Virtually any agent can be screened according to the methods of this invention. Such agents include, but are not limited to nucleic acids, proteins, sugars, polysaccharides, glycoproteins, lipids, and small organic molecules. The term small organic molecules typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487-493, Houghton et al. (1991) *Nature,* 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539, 083) antibody libraries (see, e.g., Vaughn et al. (1996) *Nature Biotechnology,* 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) C&EN, Jan. 18, page 33, isoprenoids U.S. Pat. No. 5,569,588, thiazolidinones and metathiazanones U.S. Pat. No. 5,549, 974, pyrrolidines U.S. Pat. Nos. 5,525,735 and 5,519,134, morpholino compounds U.S. Pat. No. 5,506,337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

High Throughput Screening

Any of the assays described herein are amenable to high-throughput screening (HTS). Moreover, the cells utilized in the methods of this invention need not be contacted with a single test agent at a time. To the contrary, to facilitate high-throughput screening, a single cell may be contacted by at least two, preferably by at least 5, more preferably by at least 10, and most preferably by at least 20 test compounds. If the cell scores positive, it can be subsequently tested with a subset of the test agents until the agents having the activity are identified.

High throuhput assays for hybridization assays, immunoassays, and for various reporter gene products are well known to those of skill in the art. For example, multi-well fluorimeters are commercially available (e.g., from Perkin-Elmer).

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Modulator Databases.

In certain embodiments, the agents that score positively in the assays described herein (e.g. show an ability to inhibit eIF4A expression and/or activity) can be entered into a database of putative and/or actual eIF4A inhibitors and/or aging inhibitors. The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intranet, data or databases stored in specialized hardware (e.g. in microchips), and the like.

Kits

In certain embodiments kits are provided for the treatment methods and/or screening methods described herein (e.g., to inhibit/slow aging, or to screen for agents that inhibit/slow aging). "Therapeutic" kits typically include a container containing one or more eIF4A inhibitors. Such kits can, optionally include instruments for formulating or administering the agent(s). Screening kits can include any of the reagents for performing the screening assays described herein. In certain embodiments, the kits comprise a construct containing a reporter gene whose expression is regulated by eIF4A or cell(s) comprising such a construct. In addition the kits typically include instructional materials disclosing means of use of the inhibitors to slow aging, or instructional materials describing how to screen for agents that slow aging. The kits can additionally include buffers and other reagents routinely used for the practice of a particular method. Such kits and appropriate contents are well known to those of skill in the art.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Figure 1B:
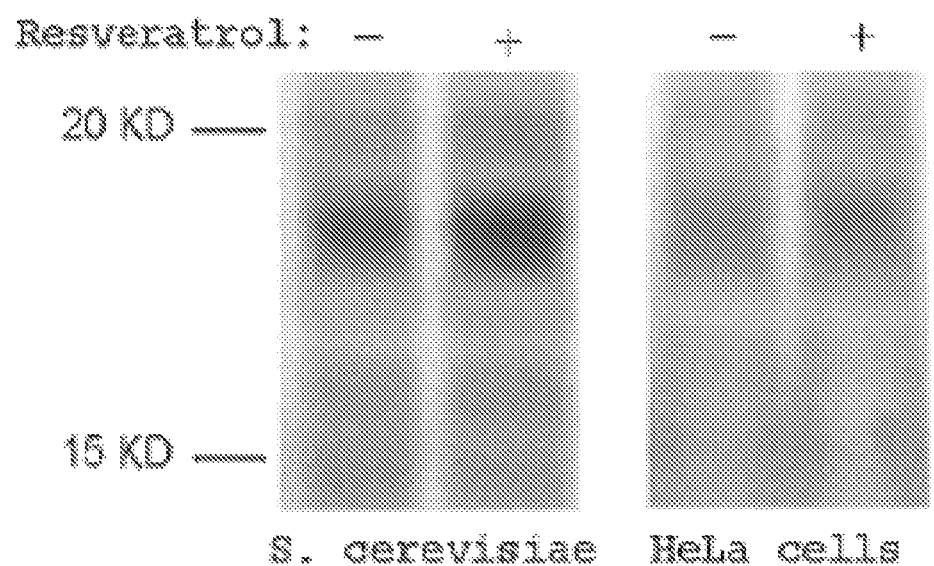
Figure 1C:
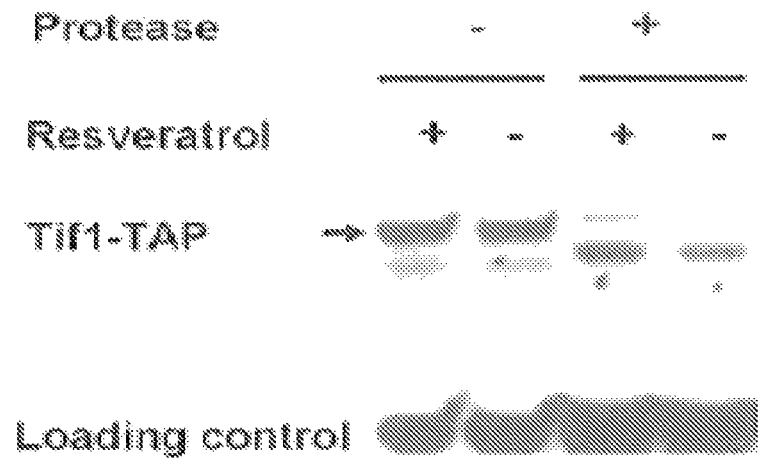

EIF4A is the Molecular Target of Certain Ageing Inhibitors eIF4A is the Molecular Target of Resveratrol We performed proteolysis on yeast cell lysates that had been incubated with resveratrol or ethanol (vehicle control). Silver staining revealed that two bands at 15 and 25 kDa were more intense in the resveratrol treated lysate (FIG. 1B).

Mass spectrometry analysis of both bands showed that eukaryotic initiation factor 4A (eIF4A) was enriched in the resveratrol-treated sample. A protected band of similar size was detected from human HeLa cell lysate (FIG. 1B), and was confirmed as human eIF4A by western blotting. The protection of yeast (TAP tagged Tif1) eIF4A by resveratrol is further confirmed by western blotting (FIG. 1C), revealing eIF4A as the real target of resveratrol in vivo.

Resveratrol Inhibits eIF4A-Dependent Translation Initiation

Resveratrol binding with translation initiation factor eIF4A suggests that the longevity drug may affect protein synthesis. To test this possibility, we performed kinetic translation assays with resveratrol in different systems.

Figure 2:
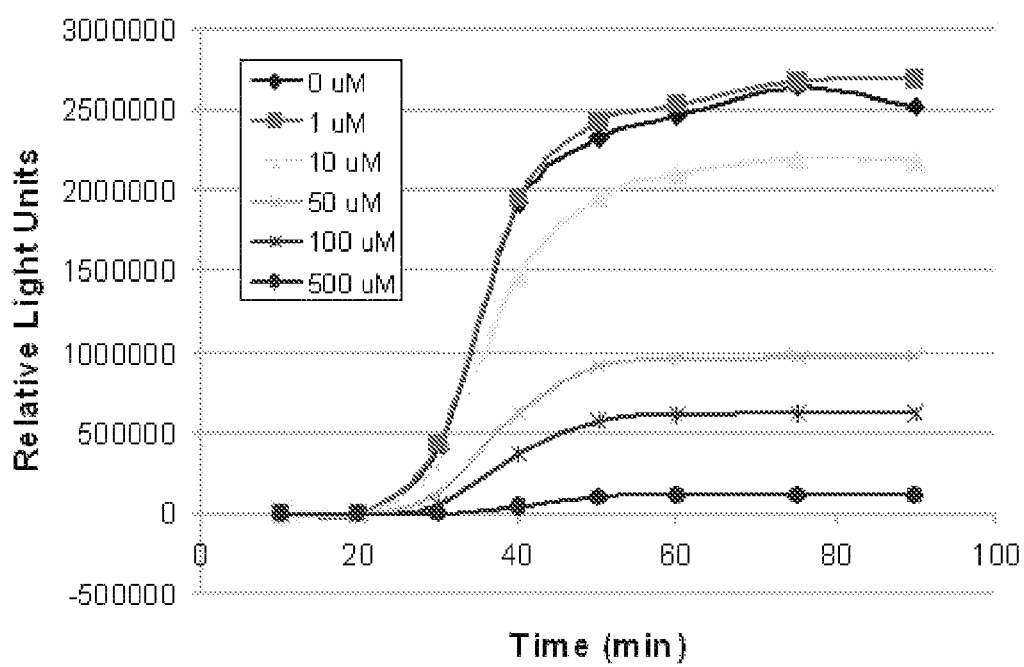
FIG. 2 shows that resveratrol inhibits eukaryotic translation in vitor. The rabbit reticulocyte lysate system was treated with different concentration of resveratrol (0, 1, 10, 50, 100, 500 µM), and the translation of firefly luciferase mRNA was measured with Promega luciferase assay.

The in vitor translation assay is performed with the rabbit reticulocyte lysate system. We added different concentrations of resveratrol into the in vitor translation reaction, and used the translation of firefly luciferase mRNA as a readout. As shown in FIG. 2, firefly luciferase signals decreased with increasing concentrations of resveratrol. Translation is reduced by >70% at 100 µM resveratrol, the concentration at which we previously detected eIF4A protection in HeLa cell lysate. This result provided the first evidence for resveratrol's inhibitory effect on eukaryotic translation.

Protein synthesis is a highly regulated process. Translation initiation in eukaryotes is usually the rate-limiting and most tightly controlled stage of polypeptide synthesis. For the majority of eukaryotic mRNAs, eIF4A is essential for the cap-dependent translation initiation (Merrick (2004) *Gene* 332: 1). Resveratrol binding to eIF4A suggests its effect on translation initiation.

To test the detailed effect of resveratrol on translation in vivo, we used a standard bicistronic dual-luciferase mRNA reporter pcDNA/Ren/HCV/FF (Bordeleau et al. (2006) *Nat. Chem. Biol.*, 2: 213-220) where translation of *renilla* luciferase is cap-dependent (i.e., eIF4A-requring), and translation of firefly luciferase is mediated by the HCV IRES which does not require eIF4A (FIG. 3A). As shown in FIG. 3B, expression of renilla luciferase was inhibited in a dose-dependent manner by resveratrol, but expression of firefly luciferase was unaffected.

Taken together, we found that resveratrol directly binds to the translation initiation factor eIF4A and inhibits eIF4A-dependent translation. It is interesting to note that previously, deletion of TIF1 or TIF2, which are duplicate genes encoding the yeast *S. cerevisiae* eIF4A, and RNAi knockdown of *C. elegans* eIF4A, have been shown to increase lifespan (Smith et al. (2008) *Genome Res.*, 18: 564). Our finding thus suggests the tempting connection that eIF4A is the molecular target of resveratrol in lifespan extension, and opens up an exciting area for investigation into eIF4A (and other translation factors) as druggable anti-aging targets. In this light, several eIF4A inhibitors have been identified recently and investigated as anti-cancer drugs (reviewed in Clardy (2006) *ACS Chem. Biol.*, 1: 17).

Example 2

The Effect of Pateamine on *C. elegans* Lifespan in Liquid Media

Wild-type N2 worms were cultured at 20° C. in S-Medium seeded with *E. coli* OP50 bacteria (6.25 mg/mL) along with FUDR (0.12 mM) and the corresponding drug treatment (0, 0.5 pM, 50 pM, 5 nM, and 500 nM pateamine A in 1.15% DMSO). L4-staged worms selected for treatment were grown on NGM plates seeded with OP50 from bleach-synchronized eggs. Prior to aliquoting the worms into wells of a 96-well plate, they were washed and resuspended in S-Medium. Approximately 100 worms were in each well containing a total solution volume of 200 μL. Each condition was replicated across the entire row, providing a sufficient number of wells to measure the survival percentage of worms from multiple wells on multiple days of the analysis. After 8 and 22 days, half of the solution was replaced with fresh media containing OP50, FUDR, and drug at the same initial concentrations. As for lifespan assessment, the number of worms in a well that are alive and dead was immediately counted after exposing only that well to UV radiation for 15 s to stimulate a response in movement. Wells exposed to radiation were not reused for data collection at a later time. Data analysis was performed with Microsoft Office Excel.

Figure 5:
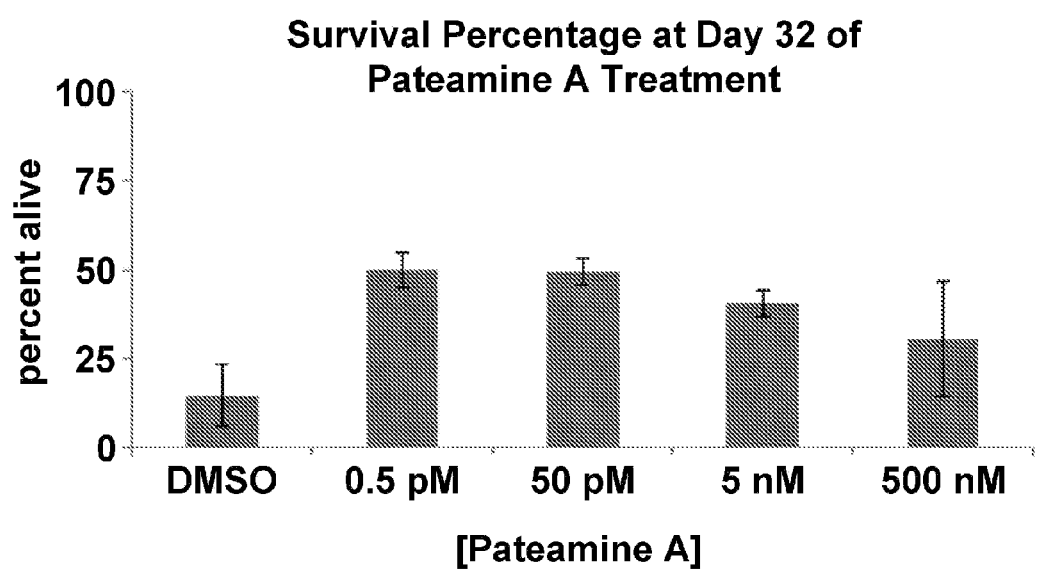
FIG. 5 illustrates the effect of pateamine on *C. elegans* lifespan. Percentages shown are averaged over three wells with error bars representing one standard deviation.

Data are shown in FIG. 5. The statistical results are shown below in Table 2.

TABLE 2

Statistical analysis of the effect of pateamine A on *C. elegans* lifespan.
T-Test Analysis (Assuming Equal Variance) of Percent Survival
Difference from DMSO at 32 Days of Pateamine A Treatment

| [Pateamine A] | p-Value |
|---|---|
| 0.5 pM | 0.004 |
| 50 pM | 0.003 |
| 5 nM | 0.009 |
| 500 nM | 0.211 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of slowing age-related muscle wasting in a human exhibiting age-related frailty characterized by sarcopenia, said method comprising:
   administering to said human a pharmaceutical formulation comprising pateamine A in an amount sufficient to inhibit expression or activity of EIF4A and to reduce the progression of said age-related muscle wasting.

2. The method according to claim 1, wherein said pateamine A is administered in a unit dosage formulation.

3. The method according to claim 1, wherein said agent is combined with an excipient suitable for administration to a human.

* * * * *